United States Patent [19]

Luca et al.

[11] 4,160,040

[45] Jul. 3, 1979

[54] FREELY-FLOWING POWDERED FRESH BAKER'S YEAST PREPARATION AND METHOD OF PRODUCING IT

[75] Inventors: Sebastiano F. Luca, Berlin; Jürgen Thommel, Delingsdorf; Walter K. Bronn, Berlin, all of Fed. Rep. of Germany

[73] Assignee: Versuchsanstalt der Hefeindustrie e.V., Berlin, Fed. Rep. of Germany

[21] Appl. No.: 782,256

[22] Filed: Mar. 28, 1977

[30] Foreign Application Priority Data

Apr. 1, 1976 [DE] Fed. Rep. of Germany ....... 2614348

[51] Int. Cl.$^2$ ..................... C12C 11/26; C12C 11/18
[52] U.S. Cl. ....................................... 426/62; 435/256
[58] Field of Search ...................... 195/65, 57, 60, 97, 195/98; 426/61, 62

[56] References Cited

U.S. PATENT DOCUMENTS

| 1,808,108 | 6/1931 | Hawks | 426/62 |
| 3,924,006 | 12/1975 | Grylls | 426/62 |
| 3,962,467 | 6/1976 | Burrows | 426/62 |

FOREIGN PATENT DOCUMENTS

| 2202153 | 10/1972 | France | 426/62 |
| 1397410 | 6/1975 | United Kingdom | 426/62 |

Primary Examiner—Thomas G. Wiseman
Attorney, Agent, or Firm—Lester Horwitz

[57] ABSTRACT

A fresh baker's yeast preparation of greater stability is provided in which a hydrophobic additive which assists in the free flow properties of moist bulk materials, for example hydrophobic silicon dioxide, is added in from 0.01 to 5% by weight of yeast optionally a hydrophilic substance can be added for example hydrophilic silicon dioxide.

2 Claims, No Drawings

FREELY-FLOWING POWDERED FRESH BAKER'S YEAST PREPARATION AND METHOD OF PRODUCING IT

Baker's yeast is generally produced and marketed in two different forms of vastly different water content, namely as fresh baker's yeast (residual water content approx. 65 to 75% by weight) and as dried baker's yeast (residual water content approx. 10% by weight or less).

Fresh baker's yeast is a yeast composition of a plastically-firm consistency from which extra cellular water has been substantially removed by mechanical extraction. It is made up for retail in various forms. Best known is the compressed yeast which is shaped into pound pieces or small domestic cubes. Also known is fresh baker's yeast in lump or coarsely granulated form; known as "bagged yeast", this form is preferred by many large scale users. When fresh baker's yeast is made up for sale in this way, it is necessary, prior to using it for baking purposes, to suspend it in water to make sure the lumpy moist yeast becomes finely dispersed and will blend evenly with the flour ("dissolving" the yeast).

In relatively rare cases, fresh baker's yeast is also marketed in the form of a liquid aqueous cellular suspension known as "yeast milk" or "liquid yeast". However, the fact that it spoils so rapidly when stored, along with other disadvantages, impair this form of presentation.

In contrast, dried baker's yeast is a yeast cell composition of more or less finely granulated or lump form which has been completely dehydrated under gentle conditions. Prior to being used for baking, most types of dried baker's yeast have to be reconstituted under special conditions with water or with aqueous solutions. Only a few types are "instant" in nature and can be added directly to the flour.

The invention is based on the problem of providing a new form of packaging for the conventional mechanically drained fresh baker's yeast so that it is suitable for despatch purposes as well as offering advantages in terms of keeping properties and use for baking purposes, and also of providing a method of producing the same.

A considerable disadvantage of fresh baker's yeast is the fact that it spoils relatively quickly when stored, its shelf life depending upon its water content. This spoilage is a consequence of the endogenous metabolic processes taking place in the yeast cells and which, after certain intracellular reserves have been consumed, lead to autolysis of the yeast. Naturally, since the endogenous metabolic rate depends upon the temperature, the yeast spoils more rapidly at higher temperatures than at low temperatures. As far as possible, therefore, fresh baker's yeast is transported and stored in a refrigerated state.

The time before onset of autolysis at a specific storage temperature used in the past to be taken mostly as a measure of the storage life of a fresh baker's yeast. However, it is now known that even while the yeast is being stored, its leavening force diminishes more or less rapidly and is almost completely lost at the onset of final spoiling, i.e. autolysis. Consequently, measurement of the leavening force of yeast at intervals during storage provides a very accurate measure of the durability of a fresh yeast. The figures contained in the ensuing part of the description concerning durability of yeast are based on measurements of leavening force during yeast storage.

The leavening force was measured in a standard dough using a fermentograph (Messrs. Brabender, Duisburg) using the method advocated by A. Harbrecht and R. Kautzmann (Die Branntweinwirtschaft 107; 507-512, 536-545, 558-562; 1967).

Many attempts to improve the keeping properties of fresh baker's yeast are known from the literature. Additions of specific hydrophilic water binding agents have been suggested with the object of reducing the water content of the yeast cells, so retarding those endogenous metabolic processes dependent not only upon the temperature but also upon the effective water activity, so improving the keeping properties of the yeast. However, none of the proposals made so far in this direction has succeeded in becoming accepted in practice. It is true that the durability of the yeast can be improved by the addition of hydrophilic water binding substances in the relatively large quantities known from the literature (added quantities of up to many times the weight of the fresh yeast), but the degree of leavening force of these yeast preparations is diminished in accordance with the proportion of weight of additives.

However, the intended purpose is not achieved by adding small quantities of the hydrophilic water binding substances already suggested for fresh baker's yeast. It can be readily demonstrated that for example an addition of 15% starch or locust bean flour to fresh baker's yeast does not significantly improve the keeping properties of the yeast.

According to the invention, it has been found that the durability of fresh baker's yeast is particularly ideally improved by intimate blending with relatively small quantities of finely powdered hydrophobic substances which are normally used in industry as lubricants to improve the free flow properties of hygroscopic bulk goods which tend to agglomerate. At the same time, the moist fresh baker's yeast is converted to a fine freely-flowing powder which can be added directly to the flour in a measured quantity when preparing dough for baking. Surprisingly, the durability-enhancing effect is reinforced by admixture of hydrophilic water binding substances in quantities which by themselves produce no significant improvement in yeast durability nor produce a freely-flowing powder.

Basically, any agents which improve the free flow of hygroscopic bulk materials are suitable as hydrophobic substances. For this purpose, various sustances are used which, as the temperature of application, are present in solid, as far as possible finely comminuted and highly disperse condition, having a water-repellant character. These substances become deposited around the particles of the particular bulk material concerned and so make it readily pourable.

According to the invention, in principle all known substances of this nature are suitable (.e.g. talcum or specific salts of higher fatty acids, such as magnesium stearate). Hydrophobic silicon dioxide in a disperse colloid state has been found to be particularly suitable. Such a product is marketed for example under the name "Aerosil R 972" by Messrs. Degussa of Frankfurt. Where the use of magnesium stearate and similar salts of higher fatty acids is concerned, nevertheless, it is important to remember that they have a readily alkalising action. In order to avoid any possible damage to the yeast which might result from this, it is necessary in such cases to add appropriate quantities of organic acids, such as for example citric acids, to neutralise the alkalising action.

The quantities of the said hydrophobic substances which have to be added to achieve pourability in and to improve the durability of fresh baker's yeast are small. According to the residual water content of the fresh baker's yeast used, it is sufficient to add 0.01 to 5% by weight (related to fresh yeast) in order to achieve the desired effects. Preferably, 0.2 to 1% by weight should be added. Table 1 shows the quantities dependent upon the residual water content of the yeast.

Table 1

Quantities of additives sufficient to produce the fresh baker's yeast preparation according to the invention, as a function of the residual water content in the fresh baker's yeast

| Residual water content of untreated yeast (% by weight) | Quantities to be added in % by weight (related to fresh yeast) | | |
|---|---|---|---|
| | Hydrophobic substances (e.g. Aerosil R 972) | Hydrophilic substances | |
| | | (Aerosil 200) | Organic swellers |
| 72 | 1.0 | 5.0 | 10.0 |
| 70 | 0.5 | 2.5 | 5.0 |
| 67 | 0.3 | 1.0 | 3.0 |

As hydrophilic additives to enhance the durability-improving effect and with the action of saving on the quantities of hydrophobic substances which have to be added, it is basically ideal to use all those substances which have a capacity for water absorption and which do not harm the yeast. For example, these include the majority of known water binding organic swellers such as possibly swelling starch, alginate or locust bean flour. But also other substances have been found suitable; particularly favourable is hydrophilic silicon dioxide marketed for example under the trade name "Aerosil 200" by Messrs. Degussa of Frankfurt.

The hydrophilic organic swellers should be added in quantities of 1 to 15% by weight (related to fresh yeast), and preferably 3 to 10% by weight. When hydrophilic silicon dioxide is used, it is sufficient to add 0.2 to 10% by weight. Preferably 1 to 5% by weight are added.

Procedurally, the coarse or lumpy yeast composition mechanically drained in rotary vacuum filters or filter presses such as are used in conventional fresh baker's yeast production, is placed in a commercially available blender in which the above-mentioned additives are converted to a freely-flowing powder by mechanical blending; particularly the hydrophobic substances greatly assist the blending process. Therefore, relatively simple blenders having slowly rotating blades or planetary mixers may be used. As far as possible, long mixing times or the application of high mechanical pressures should be avoided, since otherwise — as with all pourable but moist bulk materials — lumpy aggregates will reform. Suitable blenders are for example the VRIECO horizontal spiral screw mixer (Messrs. Wendel KG, Budingen) or batch mixers of type FM or FKM (Messrs. Lodige, Paderborn). For a simple but nevertheless convincing experiment to establish the effect of this invention, it is also sufficient to place a fresh baker's yeast (particularly a "bagged" yeast) into an ordinary laboratory mortar, add one of the above-mentioned hydrophilic and hydrophobic substances and then to mix the composition with the pestle of the mortar and without applying any great force.

Comminution of the fresh baker's yeast preparation in the blender should preferably be carried out down to a maximum size of approx. 0.8 mm particle diameter. By screening out the coarser particles and returning them to the blender, this is relatively easy to achieve. The individual size of the yeast preparation particle natually influences the blending properties of the preparation with the flour when the yeast is used for baking. The smaller the yeast particles are, the more regularly and finely they can be blended with the flour when the dough is being prepared. However, this is not a deciding factor because by reason of the high shear stresses which arise when dough is being kneaded, the now water-repellant yeast particles are further comminuted. Consequently, when the yeast preparation according to the invention is used for baking, in spite of the fact that it is mixed with the flour directly and without any previous "dissolution", an equally good leavening force and equally good texture will be achieved when compared with untreated starting yeast, normally added to the dough after being "dissolved".

When a fresh yeast preparation prepared according to the invention is viewed under a stereoscopic microscope, with illumination, a unique effect is observed. It is possible quite clearly to differentiate between heavily water-bonded hyaline particles and other yellowy-creamy particles containing mainly yeast. If by means of stereomicroscopic observation, a number of the clearly visible hyaline particles are picked out from the yellowy-creamy particles, then a chemico-analytical check will show that treating the fresh baker's yeast in accordance with the invention has produced a compartmentation of the water. The majority of the extra-cellular water balanced with the intra-cellular water is separated from the yeast particles and both types of particles are obviously enclosed by the hydrophobic additive. The hydrophilic additives involved in the water compartmentation process are preferably located in those particles which are rich in water.

The figures given in Tables 2 and 3 show the improvement in keeping properties of fresh baker's yeast, achieved by the method of the invention.

The invention will be explained in greater detail hereinafter with reference to the following non-limitative examples.

EXAMPLE 1

100 g lump fresh baker's yeast ("bagged yeast") with a water content of 70% by weight, are placed in a porcelain mortar of normal laboratory type and 2.5 g hydrophilic silicon dioxide (Aerosil 200, Degussa) and at the same time 0.5 g hydrophobic silicon dioxide (Aerosil R 972, Degussa) are added, whereupon the materials are mixed by hand using the pestle and without applying any considerable force. Within a few minutes, the mixture assumes the state of a very fine and free-flowing powder.

In comparison with the starting yeast, the fresh baker's yeast preparation which is produced in this way exhibits a substantially improved durability when stored. The leavening force and the durability of the preparation are shown in Tables 2 and 3. When used for baking purposes, the fresh baker's yeast preparation is added directly to the flour while the dough is being prepared.

EXAMPLE 2

2 kg fresh baker's yeast with a moisture content of 70% by weight and 50 g hydrophilic silicon dioxide (Aerosil 200, Messrs. Degussa) are mixed for 1 minute in a blender type PMA 20 made by Messrs. Alexanderwerk of Remscheid. After addition of 10 g hydrophobic silicon dioxide (Aerosil R 972, Messrs. Degussa), blending is resumed for another minute. During the mixing process, the preparation assumes the form of a very fine and freely-flowing powder. The leavening force and durability as well as the baking application are in accordance with the fresh baker's yeast preparation produced according to Example 1.

EXAMPLE 3

100 kg fresh baker's yeast (moisture content 70% by weight) are mixed with 5 kg swelling starch and 0.7 kg hydrophobic silicon dioxide for 1 minute in a mixer operating on the centrifugal and rolling process and made by Messrs. Lodige of Paderborn, type FM 300 D. The mixture is then screened and that fraction of less that 0.8 mm mesh is used as the end product. The fraction larger that 0.8 mm is returned to the mixture for further comminution. Leavening force and durability of the preparation are shown in Tables 2 and 3.

The fresh baker's yeast preparations according to the invention are characterised not only by excellent durability and storage capacity, but can also be despatched over considerable distances by virtue of the way in which they are presented.

Table 2

Durability of the fresh baker's yeast preparation according to the invention when stored at 25° C. compared with the starting a fresh baker's yeast used

|  | Leavening force before commencement of storage (ml $CO_2$/2 h) | Storage time (weeks) | | |
| --- | --- | --- | --- | --- |
|  |  | 1 | 2 | 3 |
|  |  | Leavening force (as % of starting value) | | |
| Untreated yeast (with 30% dry yeast substance) | 1280 | 80 | 20 | — |

Table 2-continued

Durability of the fresh baker's yeast preparation according to the invention when stored at 25° C. compared with the starting a fresh baker's yeast used

|  | Leavening force before commencement of storage (ml $CO_2$/2 h) | Storage time (weeks) | | |
| --- | --- | --- | --- | --- |
|  |  | 1 | 2 | 3 |
|  |  | Leavening force (as % of starting value) | | |
| Yeast + 0.5% Aerosil R 972 + 2.5% Aerosil 200 | 1240 | 92 | 78 | 56 |
| Yeast + 0.7% Aerosil R 972 + 5.0% swelling starch | 1205 | 84 | 45 | 27 |

Table 3

Durability of the fresh baker's yeast preparation according to the invention when stored at 6° C. compared with the starting fresh baker's yeast used

|  | Storage time (weeks) | | | | |
| --- | --- | --- | --- | --- | --- |
|  | 8 | 16 | 24 | 32 | 40 |
|  | Leavening force (as % of initial value) | | | | |
| Untreated yeast (with 30% HTS) | 80 | 40 | 8 | 0 | 0 |
| Yeast + 0.5% Aerosil R 972 + 2.5% Aerosil 200 | 90 | 78 | 69 | 65 | 60 |
| Yeast + 0.7% Aerosil R 972 + 5.0% swelling starch | 91 | 75 | 59 | 47 | 36 |

(Leavening force before commencement of storage as in Table 1)

We claim:

1. A free-flowing powdery baker's yeast preparation which consists of a mixture of finely dispersed yeast, having a residual water content of 65 to 75% by weight with 0.01 to 5.0% by weight related to the yeast of hydrophobic silion dioxide in colloidally dispersed form and with 0.2 to 10.0% by weight related to the yeast of hydrophilic silicon dioxide in colloidally dispersed form, said preparation having a better stability of its fermentation activity during storage compared with compressed yeast of the same residual water content.

2. A yeast preparation according to claim 1, wherein the hydrophobic silicon dioxide comprises 0.2 to 1.0% by weight related to the yeast having a residual water content of 65 to 75% by weight and the hydrophilic silicon dioxide comprises 1 to 5% by weight related to the said yeast.

* * * * *